(12) United States Patent
Edwards et al.

(10) Patent No.: US 6,315,776 B1
(45) Date of Patent: Nov. 13, 2001

(54) THIN LAYER ABLATION APPARATUS

(75) Inventors: Stuart D Edwards, Portola Valley; Kee S Lee, Daly City; James Baker, Palo Alto; Bruno Strul, Portola Valley, all of CA (US)

(73) Assignee: Vidacare, Inc., Sunnyvale, CA (US)

( * ) Notice: Subject to any disclaimer, the term of this patent is extended or adjusted under 35 U.S.C. 154(b) by 0 days.

(21) Appl. No.: 09/338,737

(22) Filed: Jun. 23, 1999

Related U.S. Application Data

(63) Continuation-in-part of application No. 09/026,316, filed on Feb. 19, 1998, now Pat. No. 6,056,744, which is a continuation-in-part of application No. 08/731,372, filed on Oct. 11, 1996, now Pat. No. 5,964,755, which is a continuation-in-part of application No. 08/319,373, filed on Oct. 6, 1994, now Pat. No. 5,575,788, which is a continuation-in-part of application No. 08/286,862, filed on Aug. 4, 1994, now Pat. No. 5,558,672, which is a continuation-in-part of application No. 08/272,162, filed on Jul. 7, 1994, now Pat. No. 5,569,241, which is a continuation-in-part of application No. 08/265,459, filed on Jun. 24, 1994, now Pat. No. 5,505,730, application No. 09/338,737, which is a continuation-in-part of application No. 08/857,323, filed on May 16, 1997, now abandoned, which is a continuation-in-part of application No. 08/815,096, filed on Mar. 12, 1997, now abandoned, which is a continuation-in-part of application No. 08/731,372, filed on Oct. 11, 1996, now Pat. No. 5,964,755, is a continuation-in-part of application No. 08/319,373, filed on Oct. 6, 1994, now Pat. No. 5,575,788, which is a continuation-in-part of application No. 08/286,862, filed on Aug. 4, 1994, now Pat. No. 5,558,672, which is a continuation-in-part of application No. 08/272,162, filed on Jul. 7, 1994, now Pat. No. 5,569,241, which is a continuation-in-part of application No. 08/265,459, filed on Jun. 24, 1994, now Pat. No. 5,505,730.

(51) Int. Cl.[7] .................................................. A61B 18/18
(52) U.S. Cl. ......................... 606/41; 607/105; 604/103.01
(58) Field of Search .................................. 606/27–31, 41, 606/42; 607/98–105; 604/96.01, 103.01, 103.02

(56) References Cited

U.S. PATENT DOCUMENTS

| | | | | |
|---|---|---|---|---|
| 5,047,028 | * | 9/1991 | Qian | 606/49 |
| 5,277,201 | * | 1/1994 | Stern | 607/98 |
| 5,348,554 | * | 9/1994 | Imran et al. | 606/41 |
| 5,443,470 | * | 8/1995 | Stern et al. | 607/98 |
| 5,462,521 | * | 10/1995 | Brucker et al. | 604/20 |

* cited by examiner

Primary Examiner—Michael Peffley
(74) Attorney, Agent, or Firm—Michael A. Glenn

(57) ABSTRACT

An ablation apparatus has an expandable member that is inserted into an organ of a body and ablates all or a selected portion of the inner layer of the organ. Electrolytic solution fills the expandable member, and the expandable member includes a plurality of apertures from which electrolytic solution flows from the expandable member. First and second fluid conduits, which can be first and second conforming members, are in a surrounding relationship to the expandable member. The second conforming member, including a conductive surface, is made of a material that provides substantial conformity between the conductive surface and a shape of the inner layer of the organ. A plurality of electrodes is positioned between the two conforming members. The expandable member serves as an insulator to RF energy. Each electrode includes an insulator formed on a surface of the electrode positioned adjacent to the second conforming member. The combination of sandwiching the electrodes between the two conforming members, and the use of two insulators, one on the electrode and the other on the expandable member, provides selectable ablation of the inner layer of the organ. A feedback device is included and is responsive to a detected characteristic of the inner layer. The feedback device provides a controlled delivery of RF energy to the electrodes.

7 Claims, 17 Drawing Sheets

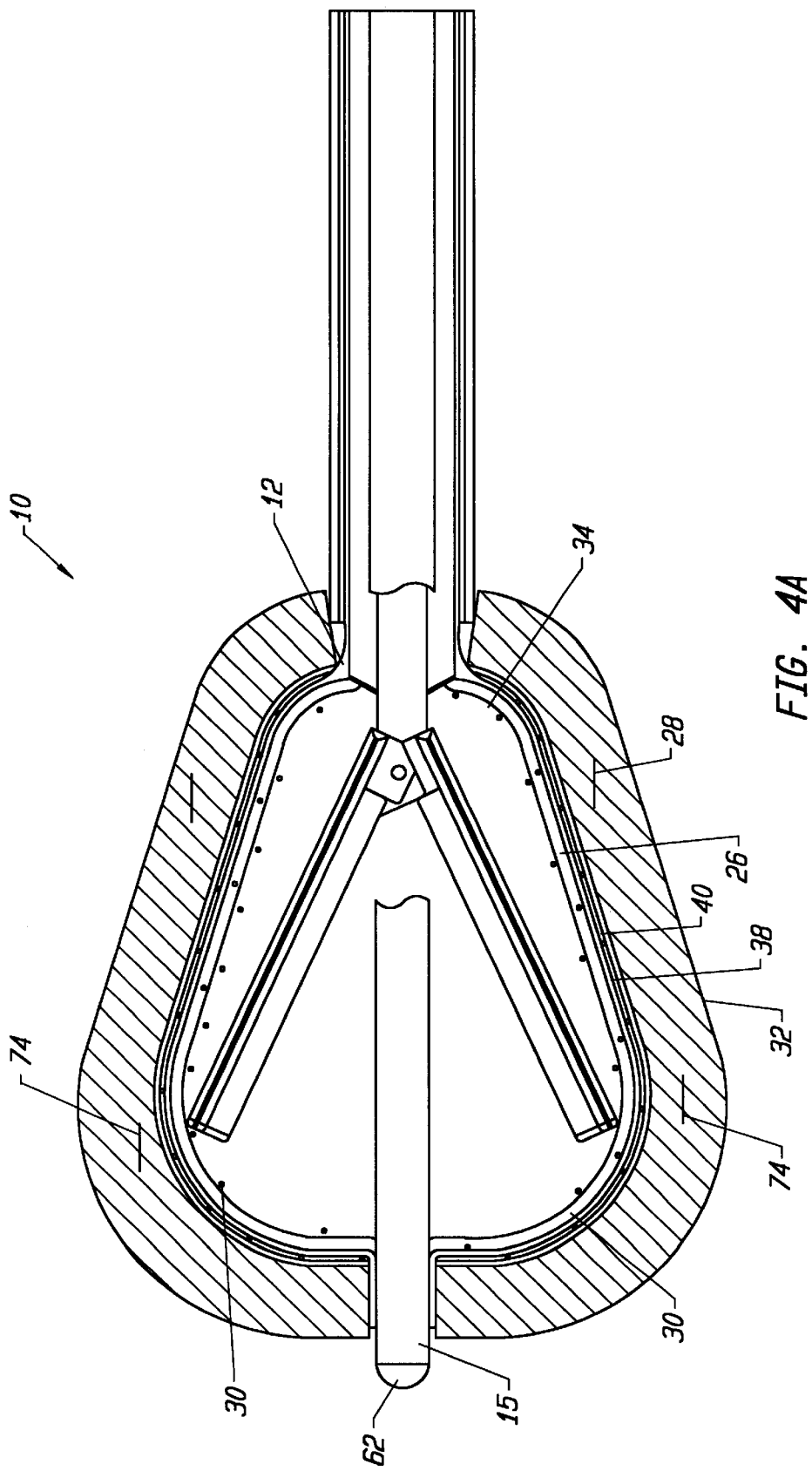

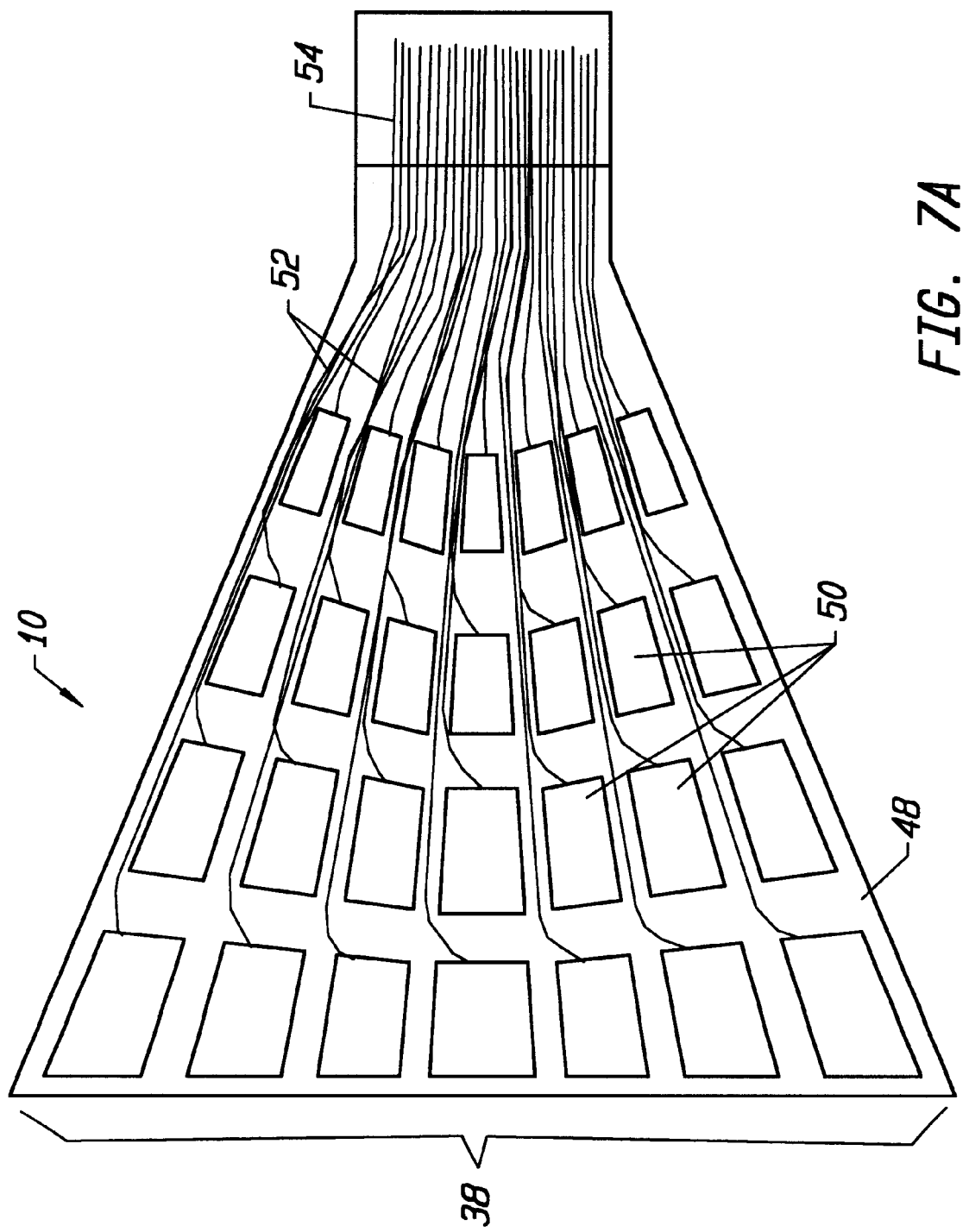

THIN LAYER ABLATION APPARATUS

RELATED APPLICATION

This application is a continuation-in-part of co-pending U.S. patent application Ser. No. 08/857,323 filed May 16, 1997, and entitled "A Radiopaque, Bioresorbable Stent, Created in Situ," (now abandoned) which is a continuation-in-part of U.S. patent application Ser. No. 08/815,096 filed Mar. 12, 1997 (now abandoned), which is a continuation in part of U.S. patent application Ser. No. 08/731,372, filed Oct. 11, 1996, now U.S. Pat. No. 5,964,755 which is a continuation-in-part of U.S. patent application Ser. No. 08/319,373, filed Oct. 6, 1994 (now U.S. Pat. No. 5,575,788), which is a continuation-in-part of U.S. patent application Ser. No. 08/286,862, filed Aug. 4, 1994 (now U.S. Pat. No. 5,558,672), which is a continuation-in-part of U.S. patent application Ser. No. 08/272,162, filed Jul. 7, 1994 (now U.S. Pat. No. 5,569,241), which is a continuation-in-part of U.S. patent application Ser. No. 08/265,459, filed Jun. 24, 1994 (now U.S. Pat. No. 5,505,730). This application is also a continuation-in-part of co-pending U.S. patent application Ser. No. 09/026,316, filed Feb. 19, 1998 and entitled "Sphincter Treatment Apparatus," now U.S. Pat. No. 6,056,744 which is a continuation-in-part of U.S. patent application Ser. No. 08/731,372, filed Oct. 11, 1996, now U.S. Pat. No. 5,964,755 which is a continuation-in-part of U.S. patent application Ser. No. 08/319,373, filed Oct. 6, 1994 (now U.S. Pat. No. 5,575,788), which is a continuation-in-part of U.S. patent application Ser. No. 08/286,862, filed Aug. 4, 1994 (now U.S. Pat. No. 5,558,672), which is a continuation-in-part of U.S. patent application Ser. No. 08/272,162, filed Jul. 7, 1994 (now U.S. Pat. No. 5,569,241), which is a continuation-in-part of U.S. patent application Ser. No. 08/265,459, filed Jun. 24, 1994 (now U.S. Pat. No. 5,505,730).

BACKGROUND OF THE INVENTION

1. Field of the Invention

This invention relates generally to an ablation apparatus for the selective ablation of the inner layers of body organs, and more particularly, to the endometrium layer of the uterus.

2. Description of Related Art

There are a number of body organs, including but not limited to the uterus, gall bladder, large intestine and the like, that have inner layers which have abnormal conditions. Traditional methods of treatment have included removal of the body organ to treat the, abnormal condition, the use of lasers, and the application of a thermal source.

A diseased condition of the uterus, menorrhagia, is defined as excessive menstrual bleeding in the absence of organic pathology. It has no known aetiology and it has been postulated that it is due to an inappropriate exposure of the endometrium to hormones. Menorrhagia is an exceedingly common problem, typically comprising approximately one in five outpatient referrals to gynecological departments. Women suffering severe menorrhagia are at risk from chronic anemia. The first treatment employed may be the administration of drug therapy. A major disadvantage is the need to administer drugs long term, and frequently the beneficial effects are only temporary. Another treatment is hysterectomy.

A number of physical and chemical methods have been tried as alternatives to hysterectomy, including the use of superheated steam, cryotherapy, urea injection and radium packing. The most commonly used methods as an alternative to hysterectomy are, ablation of the endometrium either by using a laser, such as a Nd:YAG laser, or the use of RF energy applied with an electrode.

Laser treatments have provided only limited success. RF is an attractive alternative. In RF heating, a conductive probe is placed within the uterine cavity and an insulated ground-plane electrode or belt is placed around the patient's midriff. RF energy is applied to the thermal probe with the external belt electrode acting as the return arm of the circuit. The electrical load presented by the RF thermal probe, patient, and external belt is matched to the output of the RF generator via a tuning unit, to form a series resonant circuit. Once tuned, the majority of the power applied to the probe is deposited into the endometrium as heat.

Current flows primarily capacitively, and an electric field is set up around the active tip of the probe. Tissue lying within the field becomes heated because of rapid oscillation of charged particles and locally induced currents.

Prior et al. have reported on the use of RF to treat menorrhagia. Power at 27.12 MHz was delivered to a probe that was placed into the uterine cavity and capacitively coupled to a second electrode consisting of a belt placed around the patient, Prior et al. , Int. J. Hyperthermia, 1991, Vol. 7, No. 2, pgs 213 to 220. The active electrode was a 10 mm diameter stainless-steel cylinder with a length of 70 mm. This method, however, did not adequately deliver RF energy to the entire endometrium. Because the endometrium has an irregular surface, it is difficult to deliver sufficient RF energy to the entire structure and effective treat menorrhagia.

However, it is desirable to have close contact between the RF conductive face and the endometrium. In U.S. Pat. No. 5,277,201 (the"'201 patent") an electroconductive, expandable balloon expands the interior of the uterus and effects electrical contact with the endometrial lining to be destroyed. The device of the '201 patent fails, however, to provide sufficient physical contact with the entire endometrium, and thus the treatment is not complete. Not only is the physical contact with the endometrium unsatisfactory, but the effective delivery of RF energy to the endometrium could be improved.

There is a need for an RF ablation apparatus that provides more suitable conformation with a lining of a body organ, such as the endometrium of the uterus. Additionally, there is a need for an ablation device which provides controlled and selectable distributed energy to a selected tissue site, such as the endometrium.

SUMMARY OF THE INVENTION

An object of the invention is to provide an ablation apparatus suitable for interior thin walled areas of body organs.

Another object of the invention is to provide an ablation apparatus that effectively conforms to the shape of the interior of a body organ.

Yet another object of the invention is to provide an ablation apparatus that includes a flexible circuit.

Still a further object of the invention is to provide an ablation apparatus that includes an electrode positioned between first and second fluid conduits that surround an expandable member housing an electrolytic fluid.

Another object of the invention is to provide an ablation apparatus that includes a plurality of electrodes, each with an insulator surrounding a portion of the electrode, to provide for the selectable distribution of RF energy to a desired surface.

Yet another object of the invention is to provide an ablation apparatus that provides selectable delivery of RF energy to a tissue site, and includes a feedback device in response to a detected characteristic of the tissue site.

Still a further object of the invention is to provide an ablation apparatus that evenly distributes energy to the endometrium, and includes a feedback device to monitor impedance and temperature at the endometrium.

Another object of the invention is to provide an ablation apparatus that includes a feedback device for the selectable delivery of RF energy to the endometrium, and the impedance or a temperature profile of the endometrium is monitored.

A further object of the invention is to provide an ablation apparatus with a feedback device for the selectable delivery of RF energy, and the apparatus includes electrodes with insulators that are formed on a portion of each electrode for the even delivery of RF energy to a selected tissue site.

Still a further object of the invention is to provide an ablation apparatus that positions electrodes with insulators between two foam structures to provide for the selectable distribution of RF energy to a desired tissue site.

These and other objects are achieved with an ablation apparatus for ablating an inner layer of an organ in the body. An expandable member, including but limited to a balloon, has an exterior surface that includes a plurality of apertures. Housed within the expandable member is an electrolytic solution that is released through the apertures. A first fluid conduit includes a back surface that surrounds the exterior of the expandable member, and an opposing front surface. The first fluid conduit provides delivery of electrolytic solution from the expandable member. A second fluid conduit, with a conductive surface, has a back side that surrounds the first fluid conduit. The second conduit is made of a material that provides substantial conformity between the conductive surface and a shape of the inner layer of the organ. The second fluid conduit delivers electrolytic solution from the first fluid conduit to the inner layer. A plurality of electrodes is positioned between the first and second conduits. Each electrode includes an insulator formed on a surface of the electrode that is adjacent to the second fluid conduit.

By positioning the electrodes between the first and second fluid conduits, and insulating the side of the electrode or flexible circuit that is adjacent to the second conduit, energy delivery from the electrodes to the inner layer is selectable. It is selectable in that the energy can be distributed evenly over the target surface, and energy delivery can be variable, depending on the condition of the selected tissue site.

The electrodes can be positioned on a support member. Additionally, the electrodes can form a flexible circuit made of a plurality of segments. It can be a printed circuit, or a plurality of individual electrodes. The expandable member can be expanded within the interior of a selected organ mechanically, or by introducing a fluid, such as an electrolytic solution, into its interior.

In one embodiment, the expandable member is a balloon. The first fluid conduit can be made of a foam. The second fluid conduit is a conforming member, which is preferably made of a foam.

Optionally included with the ablation apparatus is a feedback device that responds to certain detected characteristics of the inner layer. In response to the detected characteristics, the ablation device then provides a controlled delivery of RF energy to the electrodes or segments of the circuit. Various detected characteristics include, impedance of a segment of the inner layer, and a temperature profile of the inner layer at a segment. The feedback device can include a controller and a multiplexer. With the multiplexer, individual electrodes or flexible circuit segments are multiplexed.

In one embodiment, the expandable member is a balloon, and the first and second conduits are made of an open cell foam. Additionally, the foam material of the conforming member is particularly pliable and suitable for conforming to the inner layer, and achieves an effective ablation of all or a part of the inner layer even when it has a very irregular surface.

The feedback device detects impedance or a temperature profile of the inner layer at the electrodes or a segment of the circuit. The amount of delivered RF energy is adjusted according to the detected impedance or temperature profile. Additionally included in the conforming member is one or more ultrasound transducers.

The conforming member provides a conductive surface that conforms to surfaces that have irregular shapes and with the feedback device, a controlled delivery of RF energy is delivered to the endometrium. The combinations of partially insulated electrodes positioned between the two fluid conduits provides for a selectable, even, non-direct delivery of RF energy. Thus, RF energy can be effectively delivered to irregular surfaces. The feedback device provides controlled delivery of RF energy based on detected characteristics of the endometrium. The ablation apparatus is multiplexed between different electrodes or circuit segments of the flexible circuit.

The ablation apparatus of the invention is suitable for ablating a variety of surfaces of body organs including but not limited to the endometrium of the uterus.

DESCRIPTION OF THE DRAWINGS

FIG. 4(a) is a cross-sectional view of the ablation apparatus of the invention with an expandable device surrounded by a conforming member.

FIG. 7(a) is a perspective view of the invention with an inflatable device and a flexible circuit that is segmented.

DETAILED DESCRIPTION OF THE PREFERRED EMBODIMENTS

Figure 1A:
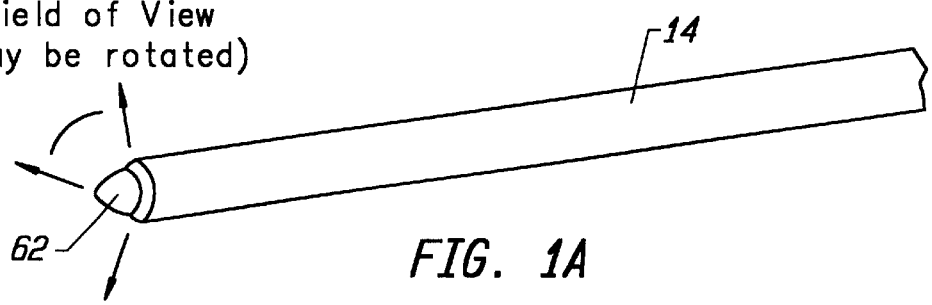
FIG. 1(a) is a perspective view of an ablation apparatus of the invention housed in an introducer sleeve and includes viewing optics.
Figure 1B:
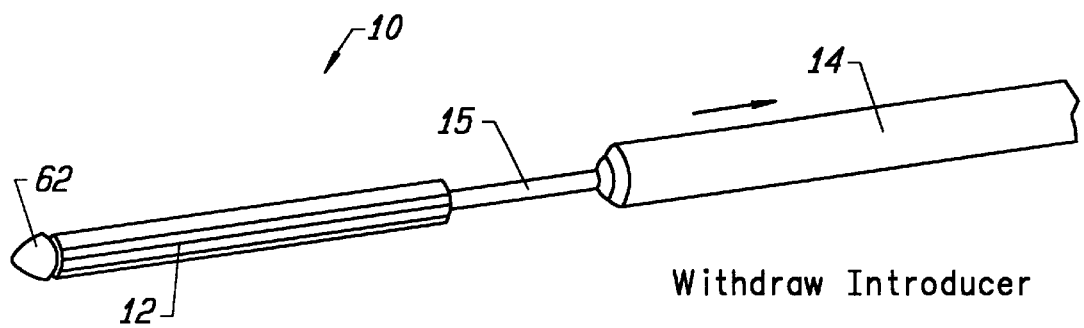
FIG. 1(b) is a perspective view of an ablation device of the invention in a non-deployed position as the introducer sleeve is withdrawn.
Figure 1C:
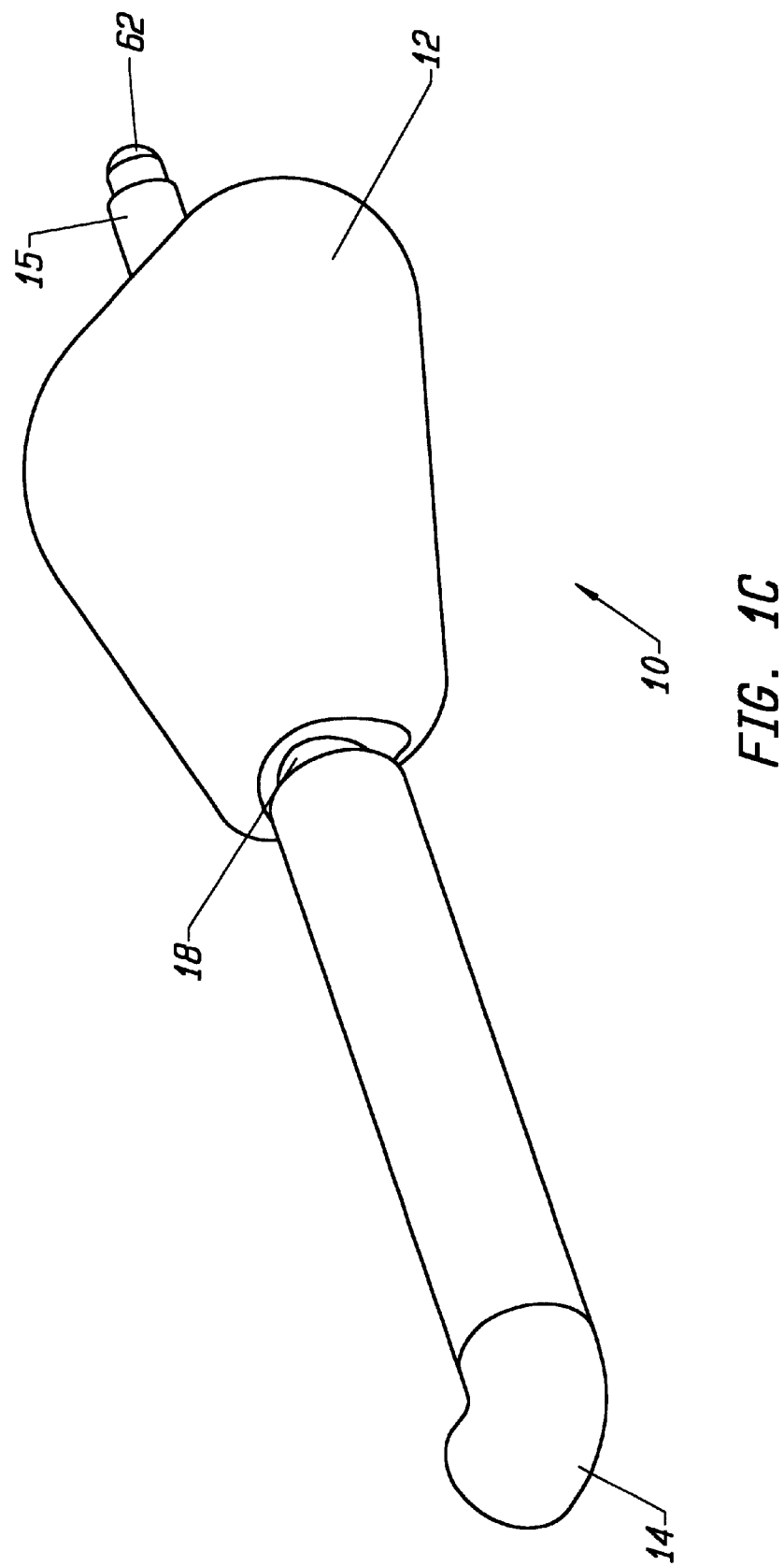
FIG. 1(c) a perspective view of an ablation device of the invention in a deployed position.
Figure 2:
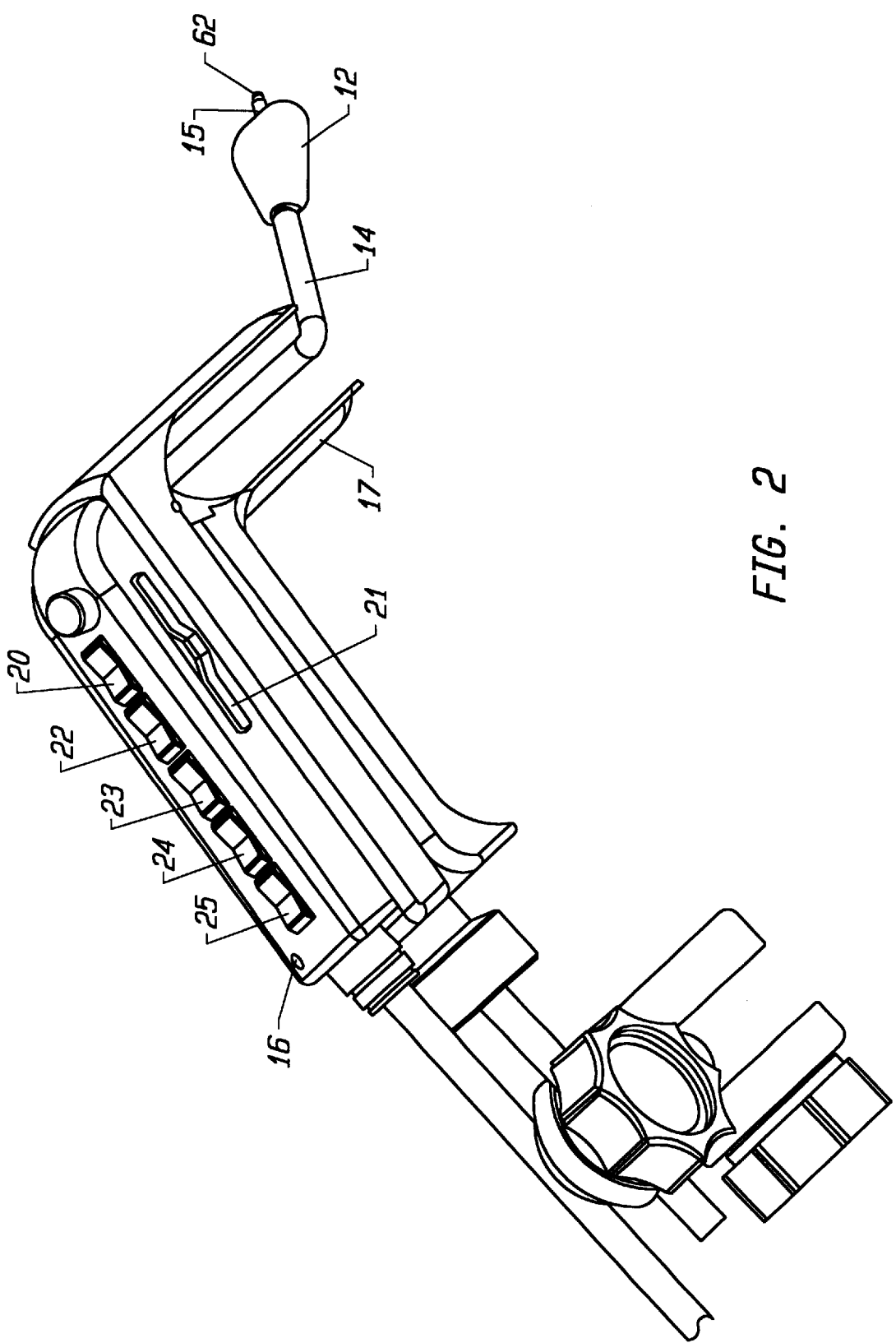
FIG. 2 is perspective view of a handle associated with the ablation device of the invention.

An ablation apparatus 10 of the invention is illustrated in FIGS. 1(a), 1(b) and 1(c) and includes an expandable member 12 that is introduced into a desired body organ through an introducer sleeve 14 which can be attached to a handpiece 16 (FIG. 2). In one embodiment of the invention, expandable member 12 is a balloon, but it will be appreciated that other devices capable of being in confined non-deployed states, during their introduction into the desired body organ or confined structure, and thereafter expanded to deployed states, can be utilized.

Expandable member 12 is rolled or folded around a core lumen 15 which contains optics, fluid paths, sensor and electronic cabling, and can be attached to a ratchet hinge 18 which imparts movement of expandable member 12 when it is in a body organ. Ablation apparatus 10 can be generally rolled or folded around a helical type of elongated structure in order to provide a wringing type of motion. Expandable member 12 is introduced through introducer sleeve 14 in a folded, or non-distended configuration. Introducer sleeve 14 can be of different cross-sectional sizes. In one embodiment, it is small enough to be introduced into the cervix under local anaesthesia, and can be on the order of about 3 mm in diameter.

Formed spring wires can be included in expandable member 12 to assist in opening it to the deployed position. Positioned on handle 16 are a variety of actuators, 20 through 25, which provide physician control of ablation apparatus 10, as more fully described hereafter. The actuators can be rocker switches, slider switches and the like. Ablation apparatus 10 is sufficiently opaque that it is visible under ultrasound.

Introducer sleeve 14 is introduced into the desired organ, as shown in FIG. 1(a), with expandable member 12 in a non-deployed configuration. Following introduction, introducer sleeve 14 is withdrawn and can be retracted into handle 16. Introducer sleeve 14 can be of conventional design, such as an introducing catheter, well known to those skilled in the art. Expandable member 12 can be swept from side to side, which movement can be imparted by hinge 18. Hinge 18 also provides for easy introduction of ablation apparatus 10 through the vagina, and into the cervix and uterus.

Generally, ablation apparatus 10 can be a mono-polar or bi-polar electrode system. It is capable of expanding so that expandable member 12 becomes inflated within a selected body organ, and RF energy is delivered to an inner lining of the organ. RF energy is passed through the inner lining or surface for a time period selected that is sufficient to achieve the desired degree of ablation. This varies depending on the body organ. RF current flows through body tissue from a return electrode, in the form of a conductive pad, applied to the patient's outer skin. Maximum heating occurs where the current density is the greatest.

In one embodiment of the invention, the body organ is the uterus, and the lining is the endometrium. It will be appreciated that the present invention is not limited to the endometrium of the uterus and that other organs, including but not limited to the general field of gynecology, can also be treated with the invention.

Electric current flowing through the endometrium causes heating due to resistance of the tissue. Endometrial ablation can be accomplished as a relatively simple medical procedure with local anesthesia.

Figure 3:
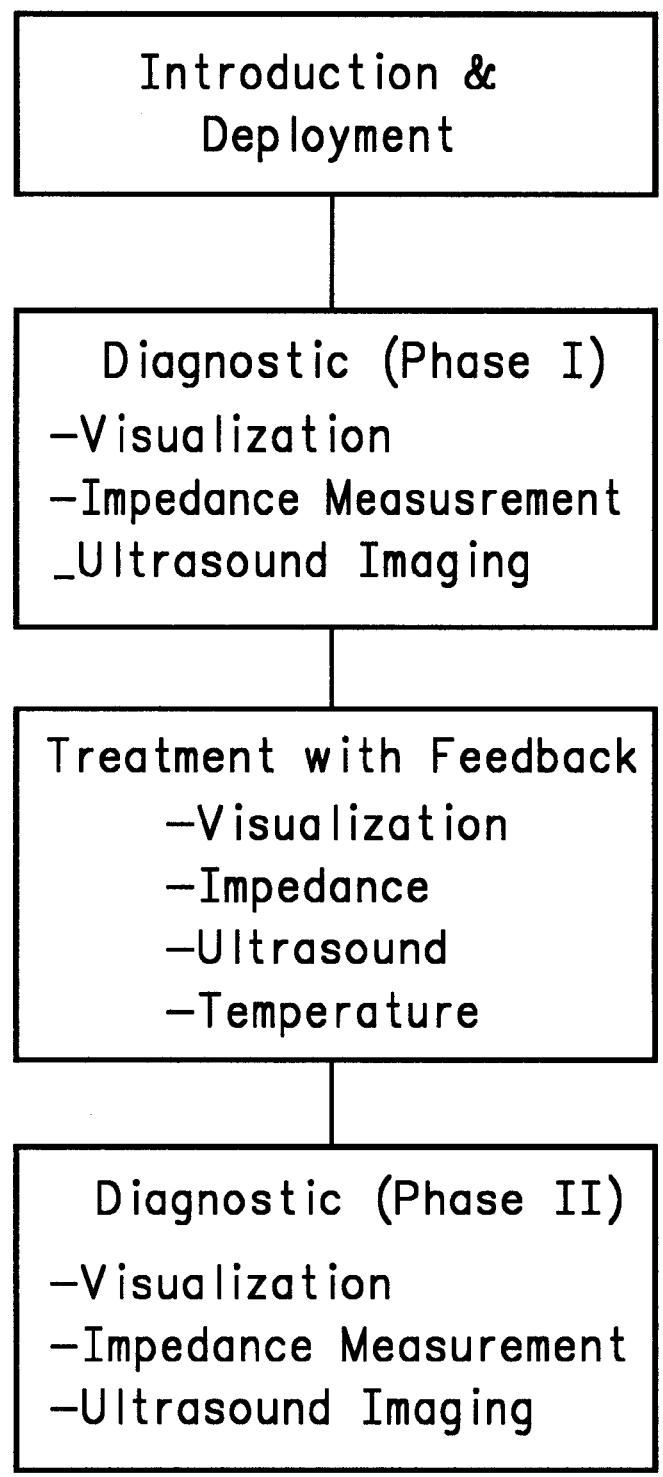
FIG. 3 is a flow chart listing the operation of the ablation device of the invention.

FIG. 3 is a flow chart illustrating the operation of ablation apparatus 10. Ablation apparatus 10 is first introduced into the uterus under local anaesthesia. Introducer sleeve 14 is then withdrawn, and expandable member 12 is expanded, either mechanically or with the introduction of a fluid or gaseous expanding medium, such as an electrolytic solution. Additionally, formed spring wires can be used in combination with a fluid to expand expandable member 12. Electrolytic solution is introduced into expandable member 12, causing it to become distended and be self-retained in the uterus.

The diagnostic phase then begins. This is achieved through a variety of mechanisms, including but not limited to, (i) visualization, (ii) measuring impedance to determine the electrical conductivity between the endometrium and ablation device 10, and (iii) the use of ultrasound imaging to establish a base line for the tissue to be treated.

In the treatment phase, the ablation of the uterus is conducted under feedback control. This enables ablation device 10 to be positioned and retained in the uterus. Treatment can occur with minimal attention by the physician. Ablation apparatus 10 automatically conforms to the interior of the uterus, provides a relatively even flow of electrolytic solution to assist in the ablation, and a plurality of discrete circuits, either in the form :of individual segments of a printed circuit, or a plurality of electrodes, are multiplexed in order to treat the entire endometrium and a portion of the myometrium. Feedback is accomplished by, (i) visualization, (ii) impedance, (iii) ultra-sound or (iv) temperature measurement. The feedback mechanism permits the turning on and off of different segments of the circuit in a desired ablative pattern, which can be sequential from one adjacent segment to the next, or it can jump around different segments. The amount of ablation can vary. However, it is desirable to ablate about 2 to 3 mm, with approximately 1 mm of the myometrium. Ultrasound can be used to create a map of the interior of the uterus. This information is input to a controller. Individual segments of the circuit are multiplexed and volumetrically controlled. The area of ablation is substantially the same for each ablation event.

Even though there are folds and crevices in the endometrium, the entire endometrium is treated and selectively ablated. The selective ablation may be the even penetration of RF energy to the entire endometrium, a portion of it, or applying different levels of RF energy to different endometrium sites, depending on the condition of the endometrium at a particular site. The depth of RF energy penetration in the endometrium is controlled and selectable.

A second diagnostic phase may be included after the treatment is completed. This provides an indication of ablation treatment success, and whether or not a second phase of treatment, to all or only a portion of the uterus, now or at some later time, should be conducted. The second diagnostic phase is accomplished through, (i) visualization, (ii) measuring impedance, (iii) ultrasound or (iv) temperature measurement.

One embodiment of ablation apparatus 10 is illustrated in FIG. 4(a). Expandable member 12 is made of a material that is an insulator to RF energy. In this embodiment, expandable member 12 is substantially surrounded by a first fluid conduit 26, which in turn is surrounded by a second fluid conduit 28. First fluid conduit receives electrolytic solution from expandable member 12, through a plurality of apertures 30 formed in expandable member 12, and passes it to first fluid conduit. Expandable member 12 is made of a material that permits controlled delivery of the electrolytic solution, and can be made of a microporous material that does not include distinct apertures 30.

First fluid conduit 26 can be a membrane, such as a microporous membrane, made of mylar, expanded PFT such as Gortex available from Gore Company, and the like. Membrane 26 is relatively strong, and sufficiently heat resistant for the amount of thermal energy that is supplied to the endometrium. Membrane 26 applies pressure, relative to the electrolytic solution, and thus assists in controlling its flow rate. First fluid conduit 26 can also be made of a foam.

First fluid conduit 26 can be a heat sealed plenum, to distribute electrolytic solution, if second fluid conduit 28 is made of a foam type of material. It is not needed if second fluid conduit is a perforated film. In this embodiment, ablation apparatus 10 conforms tightly with the interior of the uterus so that all, or almost all, of the endometrium is in contact with a conductive surface 32 of second fluid conduit. In this case conforming member 28 is fitted into the entire uterus and expandable member 12 does not have to be moved about the uterus to complete the treatment. Alternatively, ablation apparatus 10 may not entirely fill the uterus and ablation apparatus 10 is then moved about the uterus in order to ablate all of the endometrium, or those sections where ablation is desired.

The second fluid conduit 28 is generally a conforming member that conforms substantially to the surface of the endometrium. This provides better conformity than the mere use of expandable member 12, and the delivery of treatment energy to the endometrium is enhanced.

While expandable member 12, with a single interior section 34, is the preferred inflatable member, it will be appreciated that inflatable member 12 can be made of different compositions or materials, with one or more open or closed cells or chambers. The plurality of such cells or chambers can be compressed or configured in a small diameter for insertion, and are then expanded after insertion to establish the desired electrical contact with the targeted surface of the endometrium.

Interior 34 contains an electrolytic solution, such as saline. The amount of electrolytic fluid in interior 34 is one of the factors for establishing the flow rate of electrolytic solution out of interior 34. Expandable member 12 can become more pressurized by increasing the amount of electrolytic solution. As electrolytic fluid enters expandable member 12, the pressure within interior 34 increases. This increases the flow rate of electrolytic solution out of apertures 30. A reduction in pressure will correspondingly reduce the flow rate.

Conforming member 28 is made of a material that suitably conforms to a surface 36 that is to be ablated, and can have a thickness in the range of about 0.01 to 2.0 cm. Conforming member 28 can be made of a foam type material. Suitable materials include but are not limited to, knitted polyester, continuous filament polyester, polyester-cellulose, rayon, polyimide, polyurethane, polyethylene, and the like. Suitable commercial foams include, (i) Opcell, available from Sentinel Products Corp., Hyannis, Mass. and (ii) HT 4201 or HT 4644MD from Wilshire Contamination Control, Carlsbad, Calif. Conforming member 28 has characteristics that make it particularly moldable and formable to irregular surfaces. In one embodiment, conforming member 28 is made of a an open cell foam, or alternatively it can be a thermoplastic film such as polyurethane, low density polyethylene, or may be a silicone rubber. Additionally, conforming member 28 can be capable of extruding conductive materials from conforming member 28 itself. Conforming member 28 can be implanted with conductive ions, and conductive surface 32 can be coated with a material that improves its conductivity. The combination of conforming member 28 and the application of the electrolytic solution through conforming member 28 provides for effective delivery of RF energy to endometrium surface 36. Conforming member 28 can be sufficiently porous to permit the passage of electrolytic solution.

Positioned between membrane 26 and conforming member 28 is a plurality of electrodes that collectively can be in the form of a flexible circuit, both denoted as 38, described in greater detail further in this specification. An insulator 40, such as nylon, polyimide, latex, Teflon and the like, is partially deposited on electrodes 38 so that a back side of conforming member 28 is insulated from the direct delivery of RF energy from that adjacent electrode. Insulator 40 prevents RF energy from electrodes 38 to pass directly from electrodes 38 through conforming member 28. Instead, RF energy is applied indirectly to the endometrium, causing a thermal affect in the tissue. RF energy from electrodes 38 arcs out through first fluid conduit 26 and then through conforming member 28. Expandable member 12 serves as a second insulator.

Figure 4B:
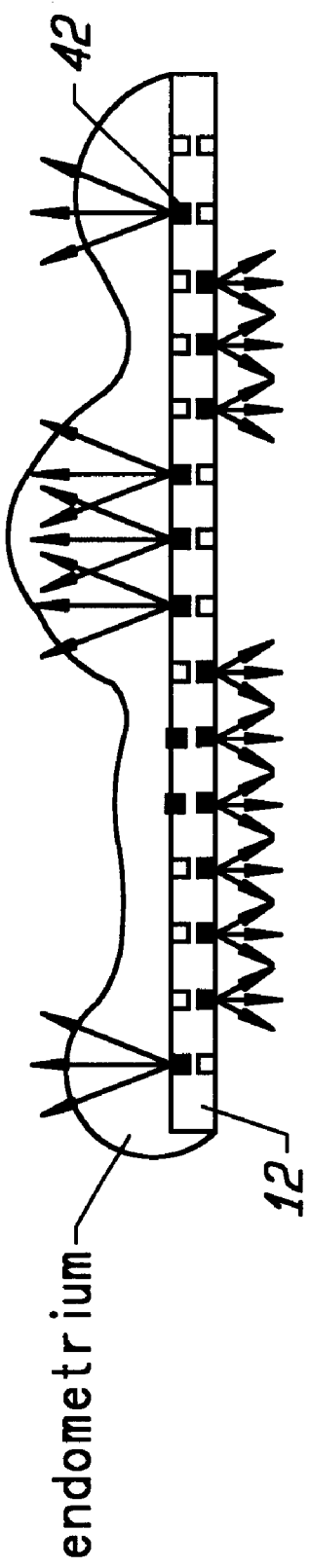
FIG. 4(b) is a perspective view of the ablative effective of electrodes positioned on a balloon without an insulator.

FIG. 4(b) illustrates the case where a plurality of electrodes 42 are positioned on an exterior surface of expandable member 12. There is direct energy delivery to the tissue. This results in an uneven penetration of energy to the endometrium. There is too much ablation for those areas of the endometrium adjacent to an electrode 42. The problem is compounded as the number of electrodes 42 adjacent to the endometrium is increased. As previously mentioned, it has been discovered that insulator 40 provides an even penetration of ablative energy.

Figure 5:
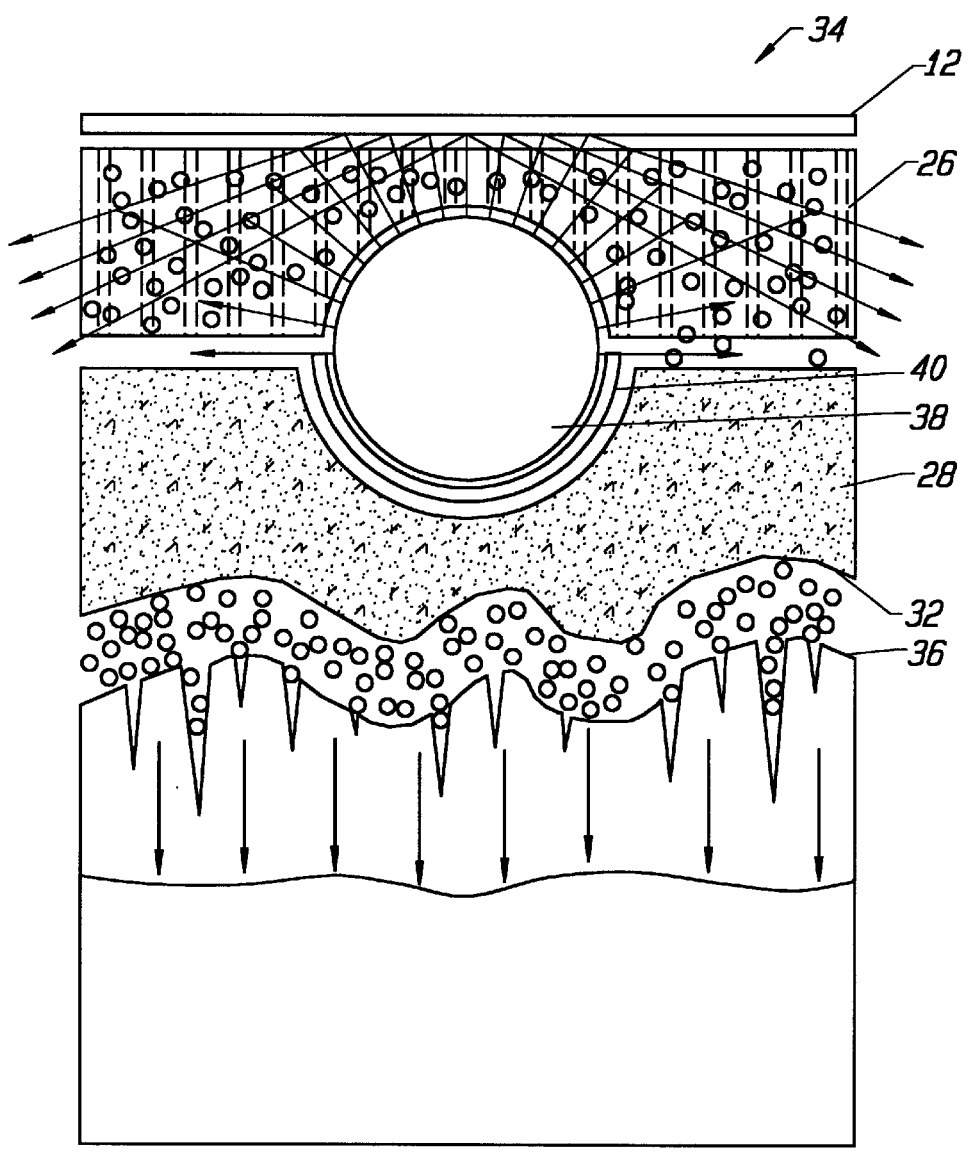
FIG. 5 is a cross-sectional view of the ablation apparatus of the invention, with a porous membrane positioned between one side of an expandable device, and a conforming foam structure that is positioned adjacent to an inner layer of an organ. A flexible circuit is positioned between the conforming foam and the porous membrane. An insulator is partially formed on the flexible circuit, or electrodes, and insulates them from the conforming member.

The relative positioning of the various members comprising ablative apparatus 10 is illustrated in FIG. 5. As shown, first fluid conduit 26 is adjacent to the exterior surface of expandable member 12, and receives electrolytic solution from the interior 34 of expandable member 12. Electrodes 38 can be positioned on a support member and form a flexible circuit. The support member can be a sheet of insulator 40, with the insulator only disposed at a place where there is an electrode 38. It is not a continuous sheet of an insulator material. Insulator 40 separates electrodes or flexible circuit 38 from conforming member 28. RF energy is delivered to electrodes or flexible circuit 38, which can be a printed circuit, or a plurality of distinct electrodes 42. Flexible circuit 38 has conforming properties sufficient to form geometrically to conforming member 28 and the endometrium.

Electrolytic solution is delivered from expandable member 12, through first fluid conduit 26 and conforming member 28, and is then delivered to the tissue to be ablated. Fluid flow is not continuous after the initial delivery of the electrolytic solution to the tissue site. First fluid conduit 26 and conforming member 28 both serve as fluid conduits. Insulator 40 is positioned so that energy from electrodes or flexible circuit 38 is evenly distributed to the endometrium.

Figure 6:
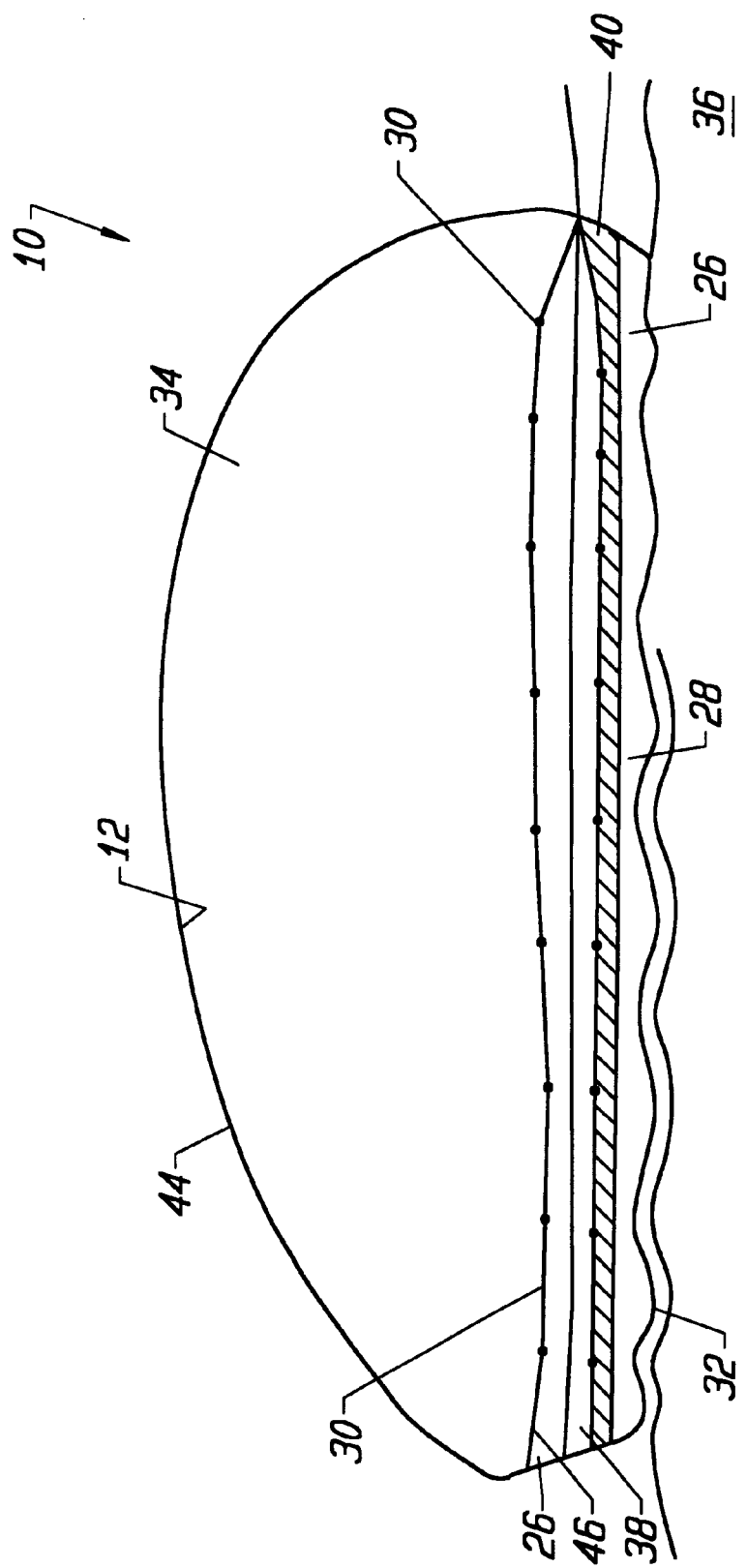
FIG. 6 is a cross-sectional view of the ablation apparatus of the invention, with a porous membrane positioned between one side of an expandable device, and a conforming foam structure that is positioned adjacent to an inner layer of an organ.

FIG. 6 illustrates another embodiment of the invention, with expandable member 12 having a back side 44, and a front side 46 that includes the plurality of apertures 30. In this embodiment, ablative apparatus 10 is moved about the interior of the uterus, and back side 44 presses against the interior surface 36 of the uterus.

As shown in FIG. 7(a) a flexible circuit 38, made of individual segments 50, can be a printed circuit that is deposited, etched or painted with a conductive ink on a support member 48. Insulation 40 is deposited on a side of each segment 50 that faces conforming member 28.

Figure 7B:
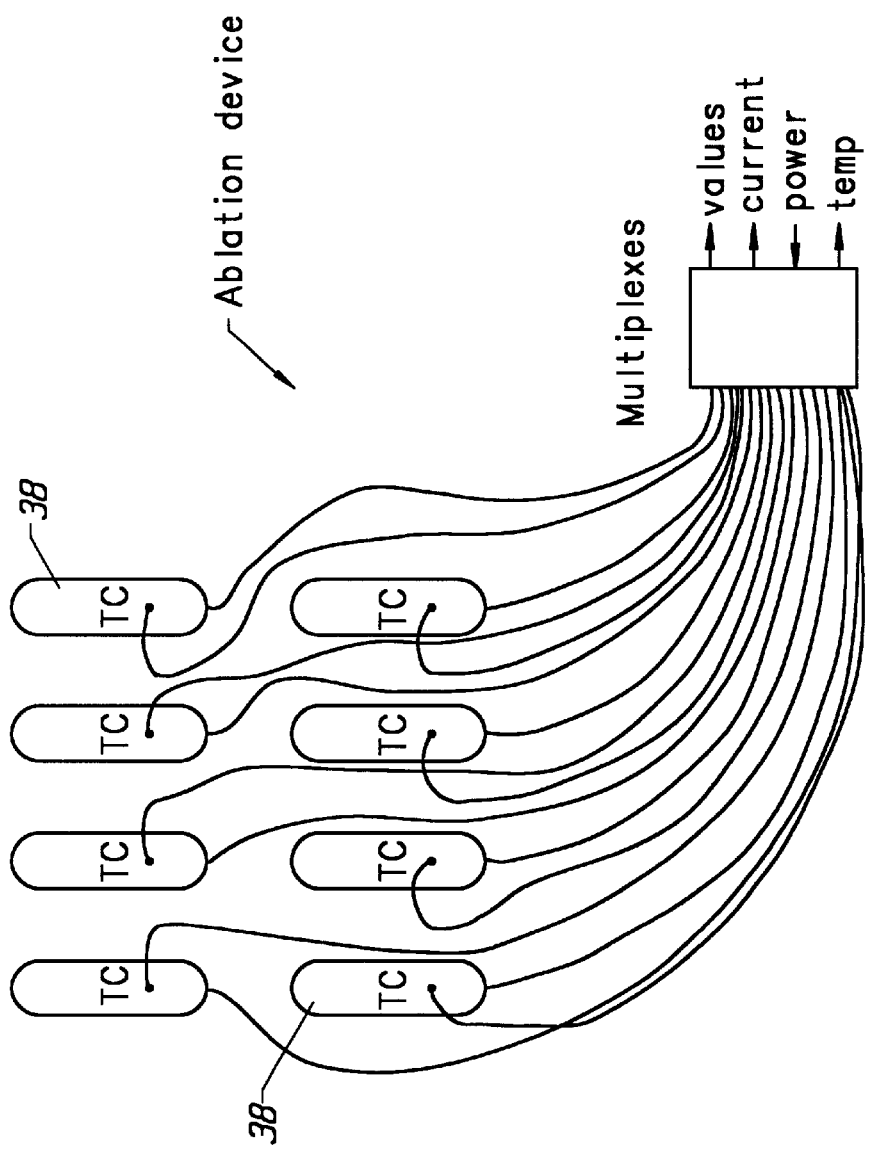
FIG. 7(b) is a second embodiment of the ablation device with individual electrodes used in place of the flexible circuit of FIG. 7(a).

Referring now to FIG. 7(b), individual electrodes 38 can be used and multiplexed in either of mono-polar or bi-polar schemes. The plurality of electrodes 38 can be positioned on a support member 48.

Figure 7C:
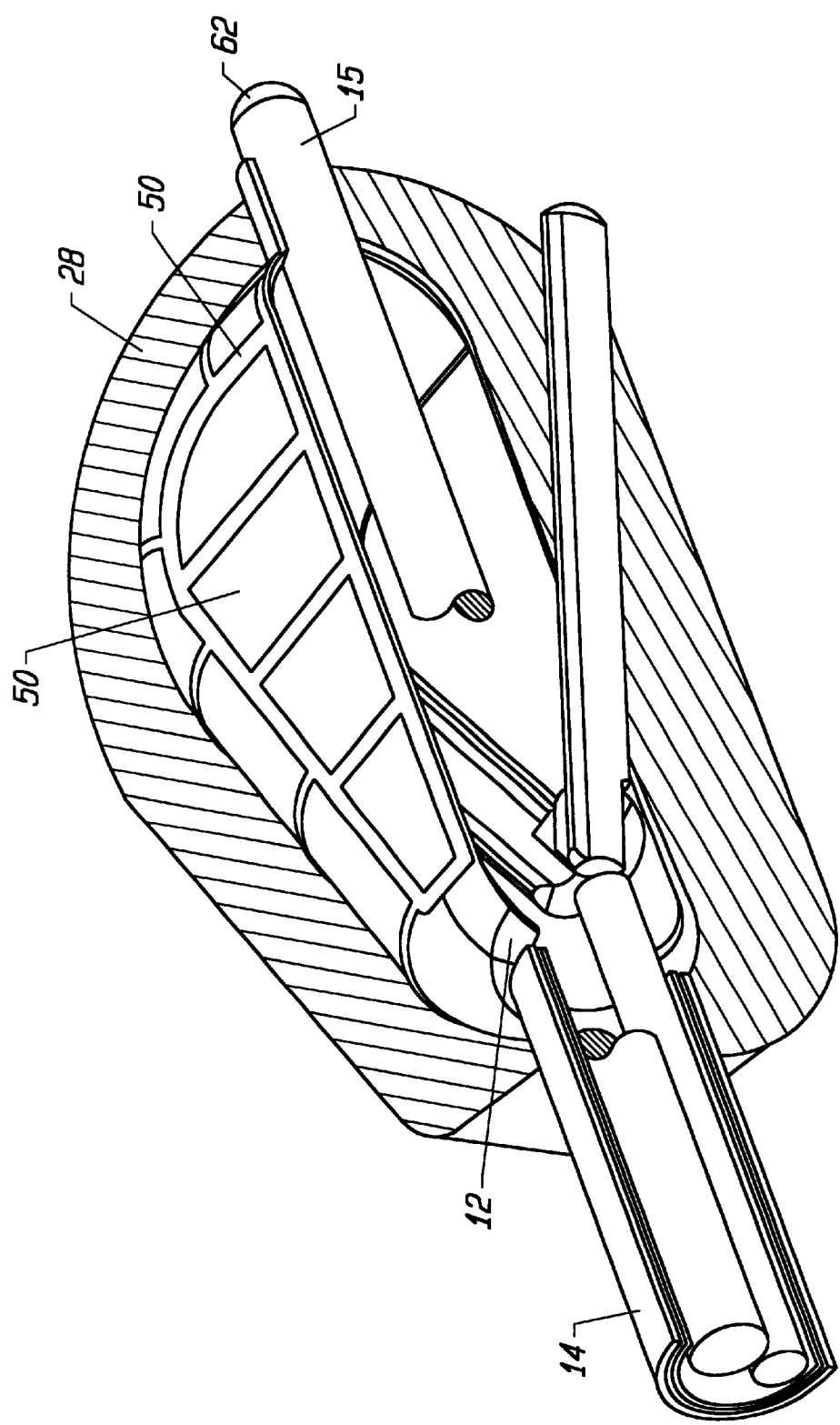
FIG. 7(c) is a perspective view of the ablation apparatus of the invention, with the flexible circuit positioned adjacent to an interior side of the conforming member. In this Figure, the insulator has been removed for ease of viewing the flexible circuit.

FIG. 7(c) shows segments 50 in a cut-away view, with insulator 40 removed in order to show the plurality of segments 50, and their relationship to expandable member 12. Electrodes 38 can also be positioned on support member 48. Printed circuit 38 can be formed by etching, deposition or lithography methods well known to those skilled in the art. Printed circuit 38 is formed of individual segments 50 and is capable of multiplexing so that only certain segments deliver RF energy at a particular time period. Although segments 50 are separated from conductive surface 32 of conforming member 28, they provide individual ablative coverage, and delivery, for the entire conductive surface 32. In this regard, the plurality of segments 50 provide ablative regions individually everywhere on conductive surface 32. Because segments 50 are not directly positioned adjacent to or on the exterior surface of expandable member 12, and with the inclusion of insulator 40 to isolate segments 50 from conforming member 26, there is a selective application of ablative energy to the endometrium.

The selectivity can be even application of RF energy everywhere it is applied to the endometrium so that the same depth of endometrium is ablated everywhere, or the amount of applied energy can be variable, depending on the characteristics of the endometrium surface. In this instance, certain sections of the endometrium will have more tissue ablated than other sections. The problems of uneven penetration of energy, shown in FIG. 4(b), are overcome by sandwiching partially insulated electrodes 38 between first fluid conduit 26 and conforming member, or foam, 28.

Figure 7D:
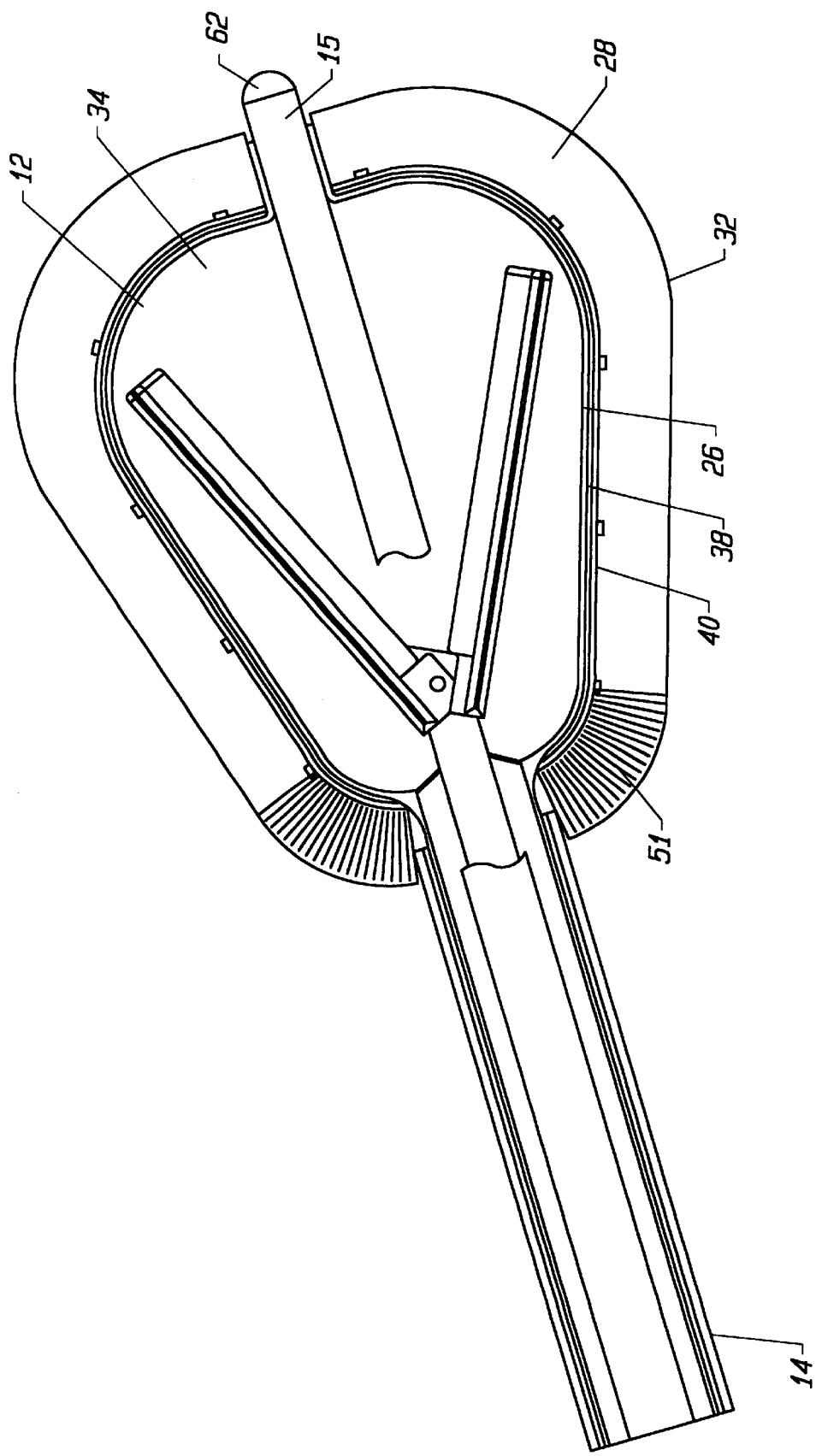
FIG. 7(d) is a cross-section view of the ablation apparatus of the invention, with the flexible or printed circuit positioned adjacent to an interior side of the conforming member, and a plurality of conductive filaments are disposed in the conforming member.

As shown in FIG. 7(d), a plurality of filaments 51 can be optionally included in conforming member 28. These help direct RF energy to conductive surface 32.

With reference again to FIG. 7(a) each segment 50 connects to a separate feedwire 52, with all of the wires going to a ribbon connector 54. First, the conductive areas are "printed" and printed circuit 38 formed. Then feedwires 52 are insulated. Each electrode 38, or segment 50 is wired with a constantan wire in order to receive RF energy from an RF energy source. A copper wire is connected to each constantan wire. This results in the formation of a T type thermocouple "TC", as illustrated in FIG. 7(b).

In one embodiment of the invention, segments 50 are about 1 $cm^2$ and are approximately 8 mm apart. Segments 50 are volumetrically controlled so that each segment ablates the same volume of the endometrium. Segments 50 are multiplexed, as more fully described hereafter.

RF power can be sequentially supplied to each electrode 38, to feedwire 52 in ribbon connector 54, or it can applied to only certain selected feedwires 52, enabling only selected electrodes 38 or segments 50 of the flexible circuit, along with the electrolytic solution, to deliver RF energy individually to the endometrium. In this way electrodes or printed circuit 38 can be multiplexed. The size of individual electrodes 38 or segments 50 included in printed circuit 38 is designed to provide the correct current density.

Figure 8:
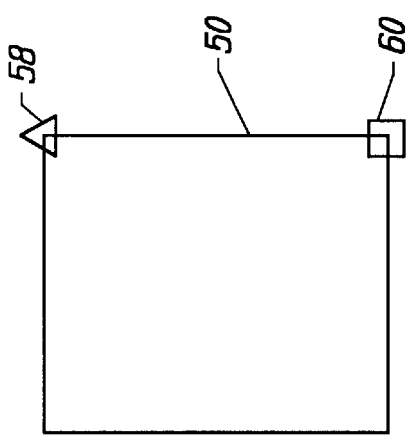
FIG. 8 is a perspective view of one of the segments of the flexible circuit shown in FIG. 7(a).

Referring now to FIG. 8, one or more impedance monitors 56 can be used to confirm, before an ablation event, that good coupling of energy is achieved. Also included is one or more temperature monitors/sensors 58. Temperature sensors 58 are conventional thermistors or thermocouples, and are positioned on electrodes or flexible circuit 38. Electrodes or flexible circuit 38 are capable of monitoring circuit continuity. Impedance is monitored between each electrode 38 or segment 50 and a ground electrode.

Figure 9:
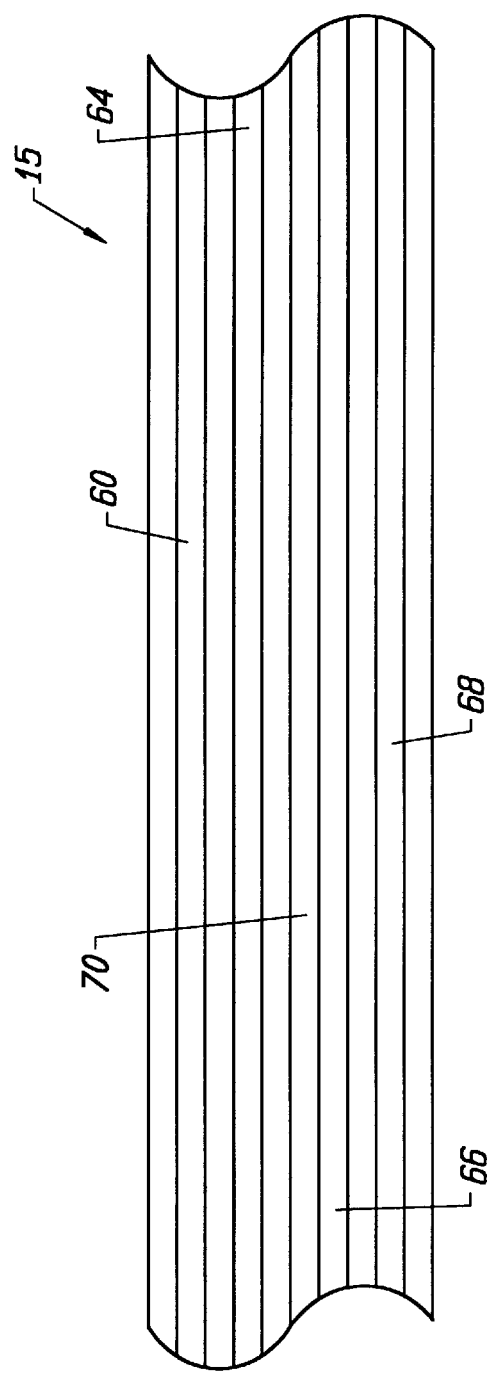
FIG. 9 is a cross-sectional view of the introducer sheath associated with the expandable device of the invention. Housed in the introducer sheath are viewing and illumination fibers, a tension wire, an RF cable, an ultrasound cable and an electrolytic solution tube.

In FIG. 9, a cross-sectional view of core lumen 15 shows that a variety of conduits, wires and fibers can be housed in the lumen. These include, but are not limited to, viewing and illumination optical fibers 60, well known to those skilled in the art, which can deliver light, such as from a Xenon source, to viewing optics 62 (FIGS. 1(a), 1(b) and 1(c); a tension wire 64 that connects to hinge 18; an RF cable 66 connecting feedwires 52 to an RF source; an electrolytic solution delivery conduit 68; and an electrical lead 70 which couples an ultrasound energy source 72 to one or more transducers 74.

Viewing optics 62 can be a 70 degree lens which permits a lateral field of view. Additionally, the combination of optical fibers 60 and viewing optics 62 can be in the form of a flexible viewing scope that is capable of providing a full field of view within the interior of the uterus.

A two-way valve is included with delivery conduit 68. A pump or other similar device advances electrolytic solution to and from expandable member 12 through delivery conduit 68. When the procedure is completed, electrolytic solution is removed from expandable member 12 through delivery conduit 68. Core lumen 15 is then rotated in a twisting type of motion, in order to helically wrap the entire ablation apparatus 10, e.g., expandable member 12, conforming member 28 and first fluid conduit 26, around core lumen 15, and substantially all of the electrolytic solution is removed. Ablation apparatus 10 is then retracted back into introducer sleeve 14. It is then removed from the uterus. Alternatively, the entire ablation apparatus 10 can be retracted directly into introducer sleeve 14.

Figure 10:
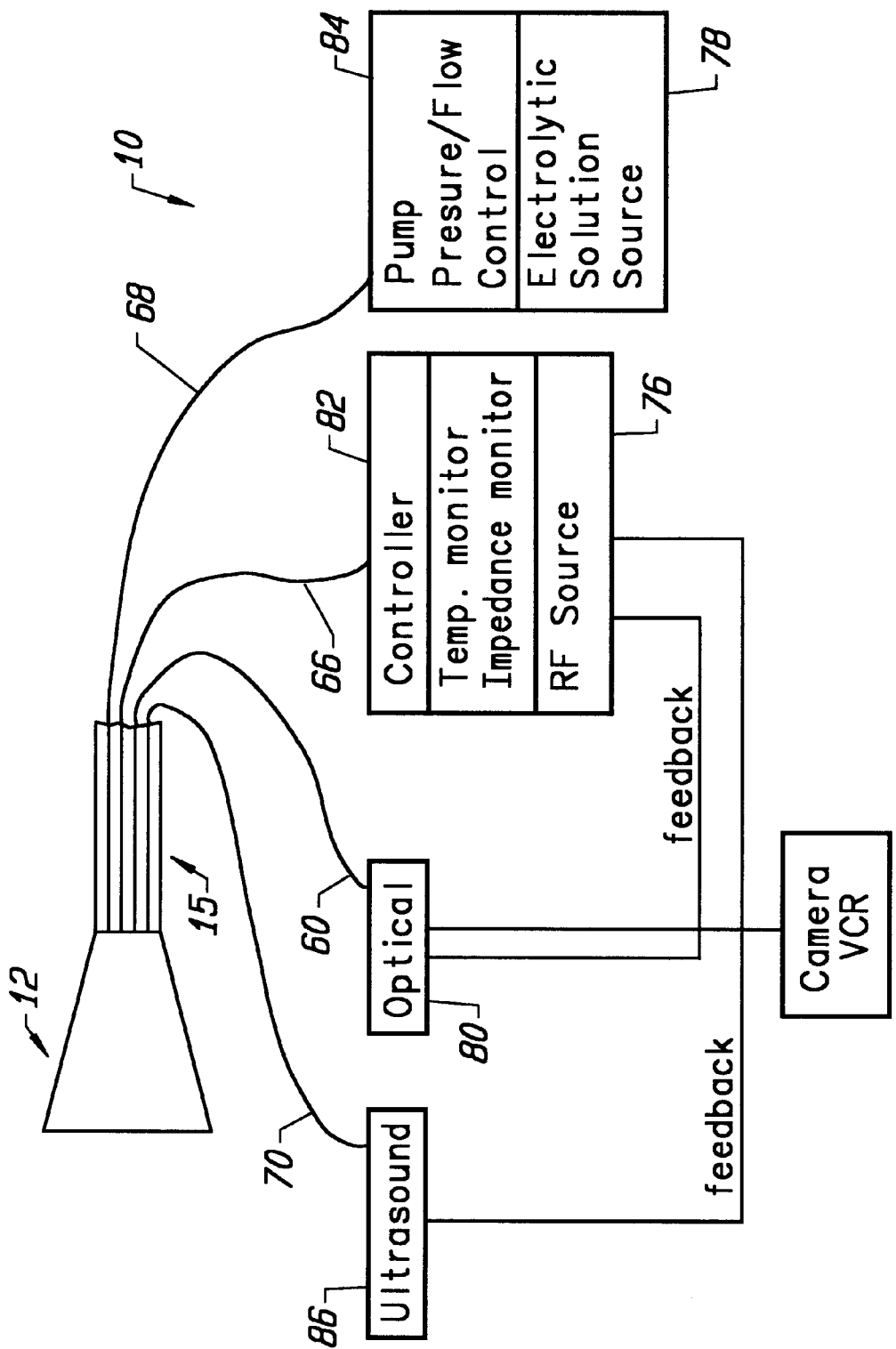
FIG. 10 is a representative block diagram of the invention showing the light, RF, ultrasound and electrolytic sources and their relationships to the expandable device.

Referring now to FIGS. 2 and 10, a rocker switch 20 operates the rotation and viewing of viewing optics 62, as well as the movement of the flexible scope. A slider switch 21 controls movement of introducer sleeve 14. Rocker switch 22 is associated with tension wire 64. It is activated to cause hinge 18 to pivot and impart mechanical movement to expandable member 12. Rocker switch 23 is operated by the physician to control the delivery, and in certain instances, the amount of RF energy from a suitable RF source 76. Rocker switch 24 controls the flow of electrolytic solution to and from expandable member 12 to an electrolytic solution source 78. Finally, a switch 25 is associated with ultrasound transducers 70. It will be appreciated that a video camera system can be associated with handle 16.

Further with regard to FIG. 10, an optical system 80 can include a light source, associated illumination and imaging fibers 60, which can be in the form of a flexible endoscope, and associated switch 20 that operates the rotation and viewing of viewing optics 62. Optical system 80 can also include an output going to a VCR, camera, and the like, and a feedback output to RF source 76 and a controller 82. RF source 76 can incorporate a controller, as well as both temperature and impedance monitoring devices. Electrolytic solution source 78 can include a pump/pressure flow control device 84, as is well known to those skilled in the art. An ultrasound source 86 is coupled to one or more ultrasound transducers 74 that are positioned in or on conforming member 28. Ultrasound transducers 74 can be positioned apart from conforming member 28. An output is associated with ultrasound source 86 and RF source 76.

Each ultrasound transducer 74 can include a piezoelectric crystal mounted on a backing material. An ultrasound lens, fabricated on an electrically insulating material, is mounted between the piezoelectric crystal and conforming member 28. The piezoelectric crystal is connected by electrical leads 70 to ultrasound power source 86. Each ultrasound transducer 74 transmits ultrasound energy through conforming member 28 into adjacent tissue. Ultrasound transducers 74 can be in the form of an imaging probe such as Model 21362, manufactured and sold by Hewlett Packard Company.

Temperature sensors 58 permit accurate determination of the surface temperature of endometrium surface 36 at conductive surface 32 adjacent to ultrasound transducers 74. Temperature sensors 58 are in thermal proximity to the piezoelectric crystals.

Figure 11:
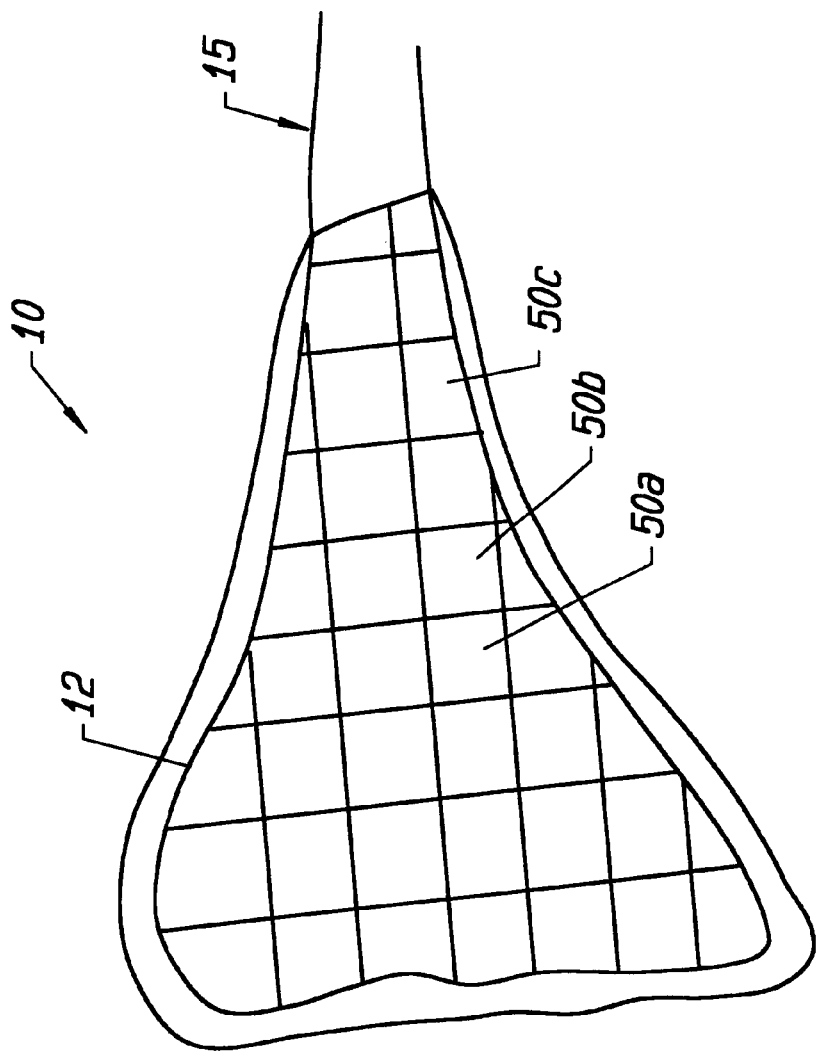
FIG. 11 is a cross-sectional diagram illustrating the relative positioning of the flexible circuit of the invention in the uterus.

As previously mentioned, ablation apparatus 10 can be used with a variety of different body organs. In FIG. 11, ablation apparatus 10 is positioned and retained in the uterus. Electrodes 38 or individual or a plurality of segments 50 can be activated to ablate the endometrium. Ablation apparatus 10 is multiplexed and delivers RF energy to only certain sections of the endometrium so that, for instance, segment 50(a) is first activated, then segment 50(b), segment 50(c) and so on. For example, each segment can provide 50 watts or less of power.

Figure 12:
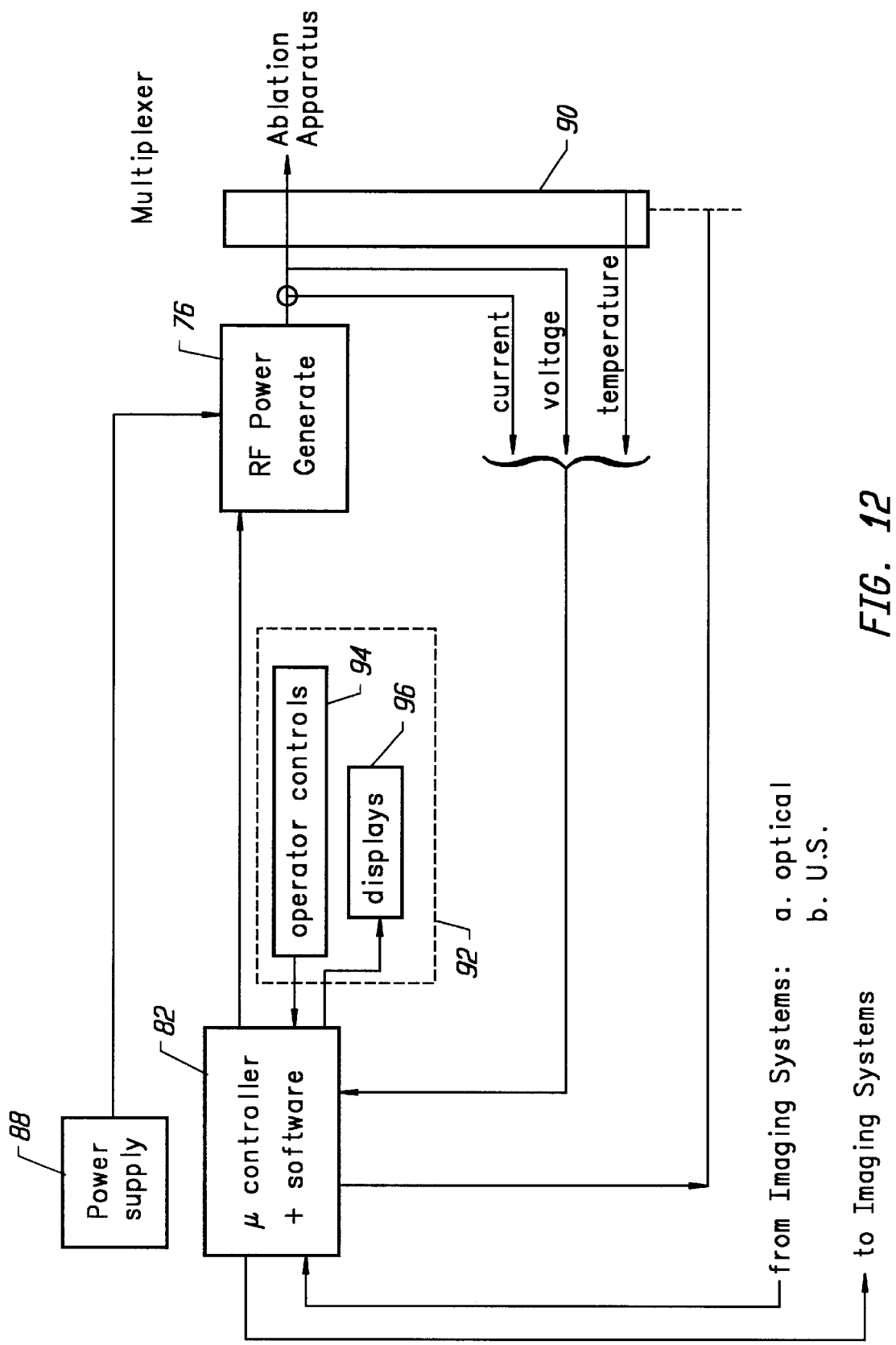
FIG. 12 is a block diagram of an ablation apparatus of the invention that includes a controller and multiplexer.

Referring now to FIG. 12, a power supply 88 feeds energy into RF power generator (source) 76 and then to ablation apparatus 10. A multiplexer 90 measures current, voltage and temperature (at the numerous temperature sensors), going to each electrode 38 or segment 50 of ablation device 10. Electrodes 38 or segments 50 are individually measured during an ablation event at that particular sensor. Multiplexer 90 is driven by controller 82, which can be a digital or analog controller, or a computer with software. When controller 82 is a computer, it can include a CPU coupled through a system bus. On this system can be a keyboard, a disk drive, or other non-volatile memory systems, a display, and other peripherals, as known in the art. Also coupled to the bus are a program memory and a data memory.

An operator interface 92 includes operator controls 94 and a display 96. Controller 82 is coupled to the imaging systems, including transducers 74, temperature sensors 58, printed circuit 38 (current and voltage), and viewing optics 62 and optical fibers 60.

Current and voltage are used to calculate impedance. Temperature and impedance are measured and then treatment can begin. Preferably, only one electrode 38 or segment 50 ablates at a time. Diagnostics are done either optically or through ultrasound. Diagnostics can be performed both before ablation of the endometrium, and also after ablation as a check to ascertain the effectiveness of the treatment.

Temperature sensors 58, and sensors contained within RF source 76, measure voltage and current that is delivered to endometrium surface 36. The output for these sensors is used by controller 82 to control the delivery of RF power. Controller 82 can also control temperature and power. An operator set level of power, and/or temperature, may be determined and this will not be exceeded. Controller 82 maintains the set level under changing conditions. The amount of RF energy delivered controls the amount of power. A profile of power delivered can be incorporated in controller 82, as well as a pre-set amount of energy to be delivered can also be profiled.

Feedback can be the measurement of impedance, temperature and occurs either at controller 82 or at RF source 76 if it incorporates a controller. For impedance measurement, this can be achieved by supplying a small amount of non-therapeutic RF energy. Voltage and current are then measured to confirm electrical contact.

Circuitry, software and feedback to controller 82 result in full process control and are used to change, (i) power (modulate)-including RF, incoherent light, microwave, ultrasound and the like, (ii) the duty cycle (on-off and wattage), (iii) mono-polar or bi-polar energy delivery, (iv) fluid (electrolyte/saline) delivery, flow rate and pressure and (v) determine when ablation is completed through time, temperature and/or impedance. These process variables can be controlled and varied based on tissue temperature monitored at multiple sites on the ablating surface, and impedance to current flow monitored at each electrode 38 or segment 50, indicating changes in current carrying capability of the tissue during the ablative process. Additionally, controller 82 can provide multiplexing, monitor circuit continuity, and/or determine which electrode 38 or segment 50 is activated.

Figure 13:
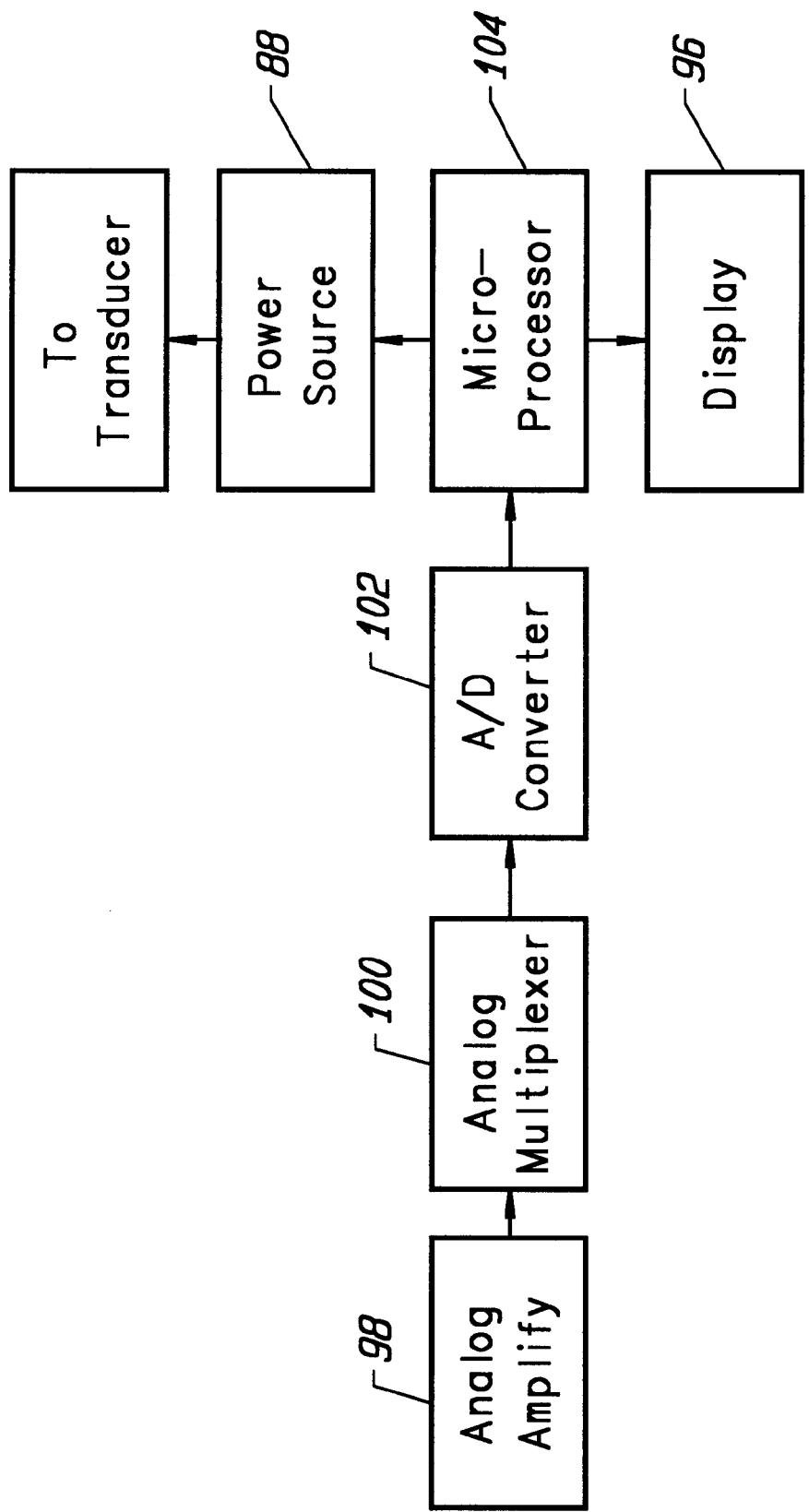
FIG. 13 is a block diagram of one embodiment of a system for processing outputs from the temperature sensors and ultrasound transducers.

A block diagram of one embodiment of suitable processing circuitry is shown in FIG. 13. Temperature sensors 58 and transducers 74 are connected to the input of an analog amplifier 98. Temperature sensors 58 an be thermistors which have a resistance that varies with temperature. Analog amplifier 98 can be a conventional differential amplifier circuit for use with thermistors and transducers. The output of analog amplifier is sequentially connected by an analog multiplexer 100 to the input of an analog to digital converter 102. The output of amplifier 98 is a voltage which represents the respective sensed temperatures. The digitized amplifier output voltages are supplied by analog to digital converter 102 to a microprocessor 104. Microprocessor 104 calculates the temperature or impedance of the tissue. Microprocessor 104 can be a type 68000. However, it will be appreciated that any suitable microprocessor, or general purpose digital or analog computer, can be used to calculate impedance or temperature.

Microprocessor 104 sequentially receives and stores digital representations of impedance and temperature at segments 50. Each digital value received by microprocessor 104 corresponds to different temperatures and impedances.

Calculated temperature and impedance values can be indicated on display 96. Alternatively, or in additional to the numerical indication of temperature or impedance, calculated impedance and temperature values can be compared by microprocessor 104 with temperature and impedance limits. When the values exceed predetermined temperature or impedance values, a warning can be given on display 96, and additionally, the delivery of RF energy to that electrode 38 or segment 50 is then multiplexed to another electrode 38 or segment 50. A control signal from microprocessor 104 can reduce the power level supplied by RF source 76, or deenergize the power delivered to a particular electrode 38 or segment 50.

Thus, controller 82 receives and stores the digital values which represent temperatures and impedances sensed. Calculated surface temperatures and impedances can be forwarded by controller 82 to display 96. If desired, the calculated surface temperature of the endometrium is compared with a temperature limit, and a warning signal can be sent to the display. Similarly, a control signal can be sent to RF power source 76 when temperature or impedance values exceed a predetermined level. The following examples illustrate the even ablation affect of ablation apparatus 10. In each example, ablation apparatus 10 was used to ablate four quadrants (Q1 through Q4) of a tissue site. It was determined that substantially even ablation was achieved at each quadrant, even with different RF energies.

| Settings | Time-min: 7.0 | Power-Watts: 9.5 | | |
|---|---|---|---|---|
| Size | L-mm | W-mm | Depth-mm | Average Power Delivered |
| Q1 | 14.43 | 11.39 | 3.22 | 9.11 |
| Q2 | 13.90 | 11.26 | 3.83 | Watts |
| Q3 | 14.34 | 12.75 | 3.43 | |
| Q4 | 16.87 | 11.60 | 3.55 | |

| Settings | Time-min: 7.0 | Power-Watts: 9.5 | | |
|---|---|---|---|---|
| Size | L-mm | W-mm | Depth-mm | Average Power Delivered |
| Q1 | 14.89 | 13.60 | 3.26 | 9.13 |
| Q2 | 15.70 | 12.68 | 3.85 | Watts |
| Q3 | 16.10 | 12.79 | 3.10 | |
| Q4 | 16.90 | 13.58 | 3.78 | |

| Settings | Time-min: 7.0 | Power-Watts: 9.5 | | |
|---|---|---|---|---|
| Size | L-mm | W-mm | Depth-mm | Average Power Delivered |
| Q1 | 15.67 | 12.41 | 3.24 | 9.09 |
| Q2 | 12.60 | 11.24 | 3.19 | Watts |
| Q3 | 13.85 | 12.49 | 3.42 | |
| Q4 | 14.87 | 10.82 | 3.37 | |

| Settings | Time-min: 7.0 | Power-Watts: 9.5 | | |
|---|---|---|---|---|
| Size | L-mm | W-mm | Depth-mm | Average Power Delivered |
| Q1 | 15.36 | 11.54 | 3.37 | 9.06 |
| Q2 | 15.12 | 10.78 | 3.18 | Watts |
| Q3 | 15.69 | 10.86 | 3.22 | |
| Q4 | 15.27 | 11.15 | 3.38 | |

| Settings | Time-min: 7.0 | Power-Watts: 9.0 | | |
|---|---|---|---|---|
| Size | L-mm | W-mm | Depth-mm | Average Power Delivered |
| Q1 | 15.04 | 10.63 | 2.71 | 8.58 |
| Q2 | 14.36 | 10.18 | 3.19 | Watts |
| Q3 | 14.68 | 11.70 | 2.78 | |
| Q4 | 15.68 | 11.61 | 3.03 | |

| Settings | Time-min: 7.0 | Power-Watts: 9.0 | | |
|---|---|---|---|---|
| Size | L-mm | W-mm | Depth-mm | Average Power Delivered |
| Q1 | 14.78 | 11.90 | 2.78 | 8.55 |
| Q2 | 14.06 | 10.67 | 2.91 | Watts |
| Q3 | 14.72 | 11.46 | 2.96 | |
| Q4 | 15.08 | 12.91 | 2.64 | |

| Settings | Time-min: 7.0 | Power-Watts: 9.0 | | |
|---|---|---|---|---|
| Size | L-mm | W-mm | Depth-mm | Average Power Delivered |
| Q1 | 14.77 | 13.62 | 2.69 | 8.60 |
| Q2 | 13.64 | 12.78 | 2.74 | Watts |
| Q3 | 14.22 | 13.31 | 2.63 | |
| Q4 | 14.42 | 13.27 | 2.92 | |

| Settings | Time-min: 7.0 | Power-Watts: 9.0 | |
|---|---|---|---|
| Size | L-mm | W-mm | Depth-mm | Average Power Delivered |

| Size | L-mm | W-mm | Depth-mm | Average Power Delivered |
|---|---|---|---|---|
| Q1 | 14.69 | 14.14 | 3.06 | 8.56 Watts |
| Q2 | 15.76 | 12.39 | 2.96 | |
| Q3 | 15.16 | 12.65 | 2.93 | |
| Q4 | 14.96 | 11.90 | 2.56 | |

| Settings | Time-min: 7.0 | Power-Watts: 8.5 | |
|---|---|---|---|

| Size | L-mm | W-mm | Depth-mm | Average Power Delivered |
|---|---|---|---|---|
| Q1 | 15.02 | 11.98 | 2.17 | 8.20 Watts |
| Q2 | 15.11 | 12.71 | 2.20 | |
| Q3 | 15.69 | 13.12 | 2.24 | |
| Q4 | 16.18 | 12.73 | 2.14 | |

| Settings | Time-min: 7.0 | Power-Watts: 8.5 | |
|---|---|---|---|

| Size | L-mm | W-mm | Depth-mm | Average Power Delivered |
|---|---|---|---|---|
| Q1 | 14.91 | 13.04 | 2.29 | 8.23 Watts |
| Q2 | 14.70 | 13.49 | 2.08 | |
| Q3 | 15.78 | 12.61 | 2.16 | |
| Q4 | 15.84 | 12.48 | 2.21 | |

| Settings | Time-min: 7.0 | Power-Watts: 8.5 | |
|---|---|---|---|

| Size | L-mm | W-mm | Depth-mm | Average Power Delivered |
|---|---|---|---|---|
| Q1 | 15.51 | 14.40 | 2.28 | 8.16 Watts |
| Q2 | 14.68 | 12.46 | 2.04 | |
| Q3 | 15.77 | 15.32 | 2.11 | |
| Q4 | 15.45 | 12.79 | 1.98 | |

| Settings | Time-min: 7.0 | Power-Watts: 8.5 | |
|---|---|---|---|

| Size | L-mm | W-mm | Depth-mm | Average Power Delivered |
|---|---|---|---|---|
| Q1 | 15.47 | 13.35 | 2.16 | 8.18 Watts |
| Q2 | 15.40 | 13.12 | 2.19 | |
| Q3 | 13.45 | 15.24 | 2.09 | |
| Q4 | 15.73 | 13.39 | 2.21 | |

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. An ablation and/or coagulation apparatus for use in delivering energy to tissue for ablation, the apparatus comprising:

an elongate tube;

a moisture permeable and/or absorbable member mounted to the tube, the tube including a plurality of aeration openings underlying the member;

a first fluid conduit having a back surface which contacts the member, a front surface opposite the back surface, and comprising a plurality of openings between the back surface and the front surface;

a conformable second fluid conduit having a back side which contacts the front surface of the first fluid conduit, a conductive front side opposite the back side, and comprising a plurality of openings between the back side and the front side;

electrodes mounted between the first fluid conduit and the second fluid conduit; and means for delivering radio frequency energy to the electrodes.

2. An ablation and/or coagulation apparatus for use in delivering energy to tissue for ablation, the apparatus comprising:

a moisture permeable and/or absorbable member;

a first fluid conduit having a back surface which contacts the member, a front surface opposite the back surface, and comprising a plurality of openings between the back surface and the front surface;

a conformable second fluid conduit having a back side which contacts the front surface of the first fluid conduit, a conductive front side opposite the back side, and comprising a plurality of openings between the back side and the front side;

electrodes mounted between the first fluid conduit and the second fluid conduit;

means for delivering radio frequency energy to the electrodes; and suction means for drawing moisture away from the member.

3. An ablation and/or coagulation apparatus for use in delivering energy to tissue for ablation, the apparatus comprising:

an elongate tube;

a moisture permeable and/or absorbable member mounted to the tube;

a first fluid conduit having a back surface which contacts the member, a front surface opposite the back surface, and comprising a plurality of openings between the back surface and the front surface;

a conformable second fluid conduit having a back side which contacts the front surface of the first fluid conduit, a conductive front side opposite the back side, and comprising a plurality of openings between the back side and the front side;

electrodes mounted between the first fluid conduit and the second fluid conduit;

means for delivering radio frequency energy to the electrodes; and suction means for drawing moisture through the tube away from the member.

4. An apparatus for intrauterine ablation, comprising:

an elongate tube;

a pad mounted to the tube and shaped to approximate the shape of a uterus;

a first fluid conduit having a back surface which contacts the pad, a front surface opposite the back surface, and comprising a plurality of openings between the back surface and the front surface;

a conformable second fluid conduit having a back side which contacts the front surface of the first fluid conduit, a conductive front side opposite the back side, and comprising a plurality of openings between the back surface and the front surface;

an array of electrodes mounted between the first fluid conduit and the second fluid conduit;

means for delivering RF energy to the electrodes to cause current flow from the electrodes to the tissue to be ablated; and means for automatically terminating the flow of current from the electrodes to the tissue once a predetermined ablation depth has been substantially reached.

5. A method for ablating tissue, comprising the steps of:

(a) providing a member, a first conduit comprising a back surface which contacts the member and a front surface opposite the back surface, a conformable second conduit comprising a back side which contacts the front surface of the first conduit and a conductive front side opposite the back side, and electrodes between the first conduit and the second conduit;

(b) positioning the second conduit in contact with tissue to be ablated;

(c) selecting a depth to which ablation is to be carried out; and (d) delivering RF energy to the tissue through select ones of the electrodes to cause ablation of the tissue to approximately the selected ablation depth and to cause automatic termination of current flow into the tissue once the selected ablation depth has been approximately reached.

6. A method for ablating tissue, comprising the steps of:

(a) providing a member, a first conduit comprising a back surface which contacts the member and a front surface opposite the back surface, a conformable second conduit comprising a back side which contacts the front surface of the first conduit and a conductive front side opposite the back side, and electrodes between the first conduit and the second conduit;

(b) positioning the second conduit in contact with tissue to be ablated;

(c) selecting a depth to which ablation is to be carried out; and (d) selecting an effective electrode spacing which would produce ablation to approximately the desired ablation depth, and delivering RF energy to select ones of the electrodes such that the spacing between the energized electrodes is substantially the selected effective electrode spacing, to cause ablation of the tissue to approximately the selected ablation depth.

7. A method for ablating tissue, comprising the steps of:

(a) providing a member, a first conduit comprising a back surface which contacts the member and a front surface opposite the back surface, a conformable second conduit comprising a back side which contacts the front surface of the first conduit and a conductive front side opposite the back side, and electrodes between the first conduit and the second conduit;

(b) positioning the second conduit in contact with tissue to be ablated;

(c) selecting a depth to which ablation is to be carried out; and (d) delivering selecting an electrode surface density which will produce ablation to approximately the desired ablation depth, and delivering RF energy to select ones of the electrodes that the electrode surface density of the energized electrodes is substantially the selected electrode surface density, to cause ablation of the tissue to approximately the selected ablation depth.

* * * * *